United States Patent [19]

Goodley et al.

[11] 4,146,729
[45] Mar. 27, 1979

[54] PROCESS FOR PREPARING POLY(ETHYLENE TEREPHTHALATE)

[75] Inventors: George R. Goodley; Donald A. Shiffler, both of Kinston, N.C.

[73] Assignee: E. I. Du Pont de Nemours and Company, Wilmington, Del.

[21] Appl. No.: 785,577

[22] Filed: Apr. 7, 1977

[51] Int. Cl.$^2$ .............................................. C07C 69/82
[52] U.S. Cl. ...................................... 560/94; 526/68; 528/309
[58] Field of Search ....................... 260/475 P; 560/94

[56] References Cited

U.S. PATENT DOCUMENTS

| | | | |
|---|---|---|---|
| 2,829,153 | 4/1958 | Vodonik | 260/475 P |
| 2,905,707 | 9/1959 | Hurt et al. | 260/475 P |
| 2,973,341 | 2/1961 | Hippe et al. | 260/475 P |
| 3,367,847 | 2/1968 | Pierson | 260/475 P |
| 3,506,622 | 4/1970 | Higgins | 260/475 P |
| 3,590,072 | 6/1971 | Leybourne | 260/475 P |
| 3,676,485 | 7/1972 | Lewis et al. | 260/475 P |
| 3,697,579 | 10/1972 | Balint et al. | 260/475 P |
| 3,787,481 | 1/1974 | Seclair et al. | 260/475 P |
| 3,927,982 | 12/1975 | Chapman et al. | 260/475 P |

FOREIGN PATENT DOCUMENTS

| | | | |
|---|---|---|---|
| 2245703 | 3/1973 | Fed. Rep. of Germany | 260/475 P |
| 1522419 | 3/1968 | France | 260/475 P |
| 51-23234 | 2/1976 | Japan | 560/94 |
| 996689 | 6/1965 | United Kingdom | 260/475 P |
| 1337751 | 11/1973 | United Kingdom | 260/475 P |

OTHER PUBLICATIONS

Perry et al., Perry's Chemical Engineers' Handbook, Fourth Edition, Sec. 22, pp. 94-102 (1963).

*Primary Examiner*—Jane S. Myers

[57] ABSTRACT

A continuous process is disclosed for direct esterification of terephthalic acid with ethylene glycol to form low molecular weight polyester with recovery of excess glycol from reaction off-gases. The terephthalic acid is mixed with an excess of glycol, the mixture is reacted at 280°–315° C. in reaction product circulated from a reactor through an external heater and back to the reactor, and reaction product is withdrawn from the reactor for polymerization to high molecular weight polyester. Vapors formed in the reactor are fed into the bottom of a rectification column where the excess glycol is recovered for direct reuse. The vapor feed is sprayed with condensate at 140°–195° C. in the bottom of the column to remove solids and maintain conditions suitable for obtaining less than 0.05 percent glycol in overhead distillate and 0.3 to 10 percent water in glycol condensate.

5 Claims, 1 Drawing Figure

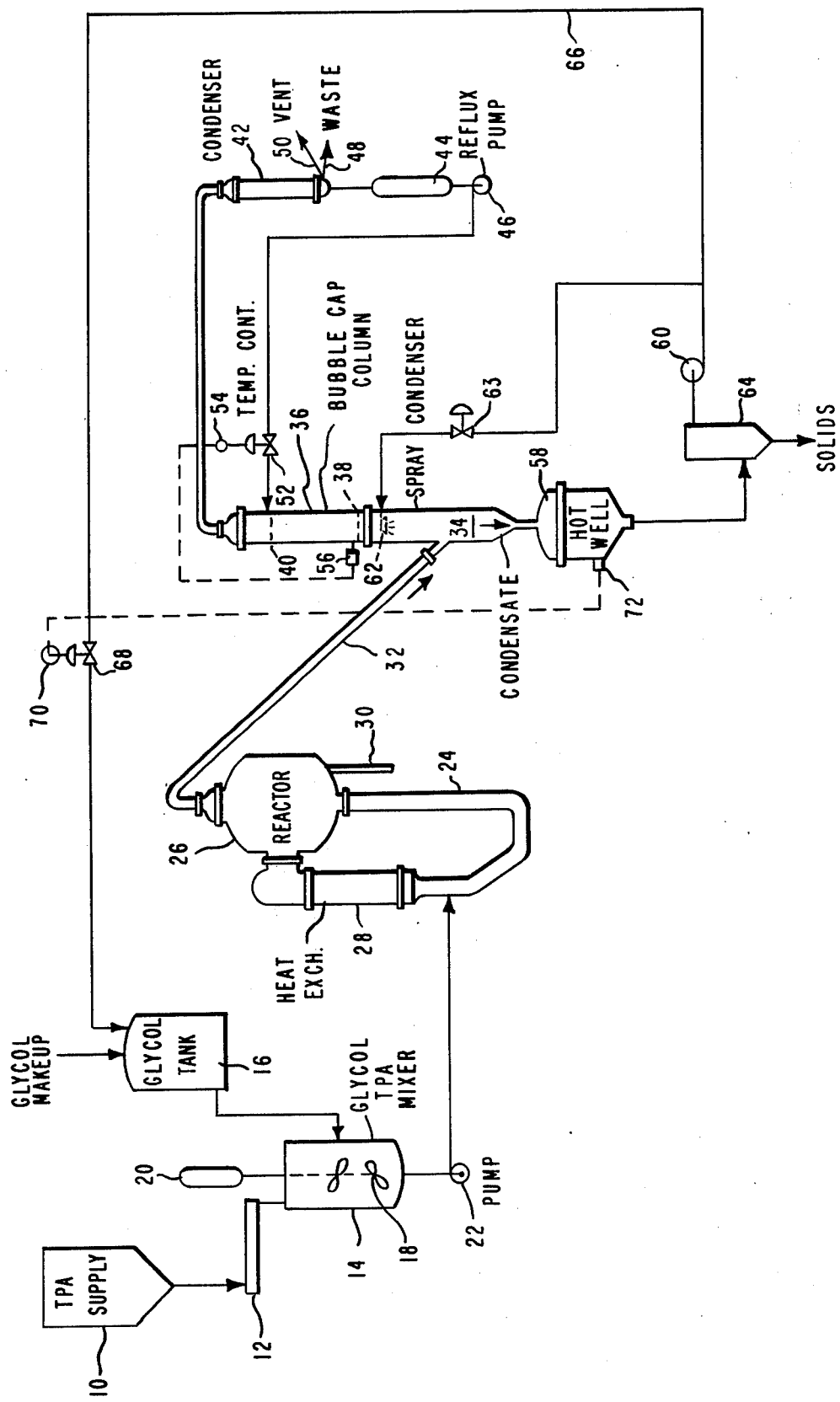

PROCESS FOR PREPARING POLY(ETHYLENE TEREPHTHALATE)

BACKGROUND OF THE INVENTION

This invention relates to a continuous direct esterification process for use in production of poly(ethylene terephthalate) from ethylene glycol and terephthalic acid, and is more particularly concerned with recovery and reuse of ethylene glycol vaporized in the esterification reaction.

Direct esterification processes for use in production of poly(ethylene terephthalate) involve esterification of terephthalic acid with ethylene glycol, followed by ester condensation polymerization. Water formed in the reactions is vaporized and removed. In a continuous process, the terephthalic acid is mixed with an excess of ethylene glycol to form a slurry or paste which is then heated to form a low molecular weight reaction product. The reaction is carried out by mixing the slurry with low molecular weight reaction product which is heated to the required reaction temperature, as illustrated in Leybourne III U.S. Pat. No. 3,590,072, Lewis et al. U.S. Pat. No. 3,676,485, Balint et al. U.S. Pat. No. 3,697,579, and Chapman et al. U.S. Pat. No. 3,927,982. The latter three patents illustrate reactors having an external heater, with reaction product circulating from the reactor vessel through the heater and back to the reactor, with the slurry being fed into the circulating product prior to the heater. All or most of the esterification reaction then takes place during passage of the glycol and terephthalic acid through the heater, and the reactor vessel serves primarily for separation of vapor from the reaction product. The low molecular weight polyester produced is fed from the reactor to subsequent polymerization steps for forming high molecular weight polymer suitable for melt-spinning into polyester yarn in conventional manner.

The excess ethylene glycol used in the slurry feed is vaporized and removed from the reactor with vapors of water and small amounts of organic impurities formed in the reaction (e.g., acetaldehyde, 2-methyl-1,3-dioxolane and 1,4-dioxane). These vapors have been condensed and processed to recover the ethylene glycol for reuse. A process for purifying the ethylene glycol is disclosed in Pierson U.S. Pat. No. 3,367,847, but a simpler and less expensive method is desirable.

The reactor vapors will also contain vaporized or entrained reaction product. The Lewis et al. patent discloses use of a partial condenser above the reactor vessel, which is operated at a temperature low enough to condense "vaporized monomer" as a liquid but now low enough to condense the ethylene glycol. The patent also discloses (column 4, lines 65-73) that a distillation column can be used in place of the partial condenser if a greater reduction in loss of monomer is desired, but there is no reference to recovery of ethylene glycol from the off-vapors.

Removal of ester product from the vapors prior to recovery of vaporized ethylene glycol is important. At the temperatures used to separate ethylene glycol from more volatile organic impurities and water formed in the reaction, ester product will form deposits which cause fouling in the recovery operation.

SUMMARY OF THE INVENTION

The present invention provides a continuous direct esterification process in which ethylene glycol is continuously recovered from reaction vapors and reused in the slurry of ethylene glycol and terephthalic acid fed to the direct esterification reaction for producing ester product. Substantially all of the ethylene glycol in the reaction vapors is recovered in a single combination spray condenser-rectification column and recycled to the feed slurry without further purification. The rectification is conducted so that the heat content of the reaction vapors supplies all of the heat required to achieve adequate distillation of water and organic impurities from the recovered ethylene glycol.

The present invention is an improvement for continuously recovering and reusing excess ethylene glycol in a continuous direct esterification process of the type wherein a slurry feed of ethylene glycol and terephthalic acid in molar proportions of 1.5 to 4 (preferably 1.8 to 3.0) of glycol to 1.0 of terephthalic acid is heated at 280° to 315° C. in reaction product to esterify the terephthalic acid and form an ester product having an average degree of polymerization of 2 to 10, and hot reaction vapors containing ethylene glycol and water plus small amounts of ester product and organic impurities are separated from the reaction product. The improvement of this invention comprises conducting the hot reaction vapors into a spray zone at the bottom of a rectification column, condensing vapors at the top of the column as an aqueous distillate, refluxing about 40 to 70 weight percent of the distillate to the column to give a distillate containing less than 0.5 percent (preferably less than 0.05%) ethylene glycol and a glycol condensate at the bottom of the column containing less than 10 percent water, spraying the reaction vapors with condensate at 140° to 180° C. (preferably 155° to 175° C.) in the spray zone to maintain steady temperature conditions and to remove ester product and a large fraction, of the glycol from the vapors, and recycling the condensate to the slurry feed.

The rectification column has 5 to 20 plates (preferably about 12 plates). The reflux is preferably adjusted to maintain a steady temperature on the bottom plate within the range of 110° to 140° C. The reaction vapors are sprayed with 1 to 25 (preferably 1 to 8) kilograms of condensate per kilogram of slurry feed to the reaction.

The column is preferably operated so that the glycol condensate contains 2 to 7 weight percent water to reduce formation of ether compounds from glycol in the esterification reaction.

The composition of the reaction vapors will depend upon the molar proportion of ethylene glycol in the slurry feed and the temperature and pressure of the esterification reaction. Preferably, the reaction is conducted at about atmospheric pressure. Typical reaction vapors contain 47 to 84 parts by weight of ethylene glycol, 53 to 16 parts water, up to 10 percent ester product, and up to 2 percent of volatile organic impurities. Most of the water and volatile organic impurities are removed in the aqueous distillate, and substantially all of the ethylene glycol and ester product are recovered in the glycol condensate.

BRIEF DESCRIPTION OF THE DRAWING

The drawing is a schematic representation of apparatus useful in the process of this invention.

DETAILED DESCRIPTION

As shown in the drawing, terephthalic acid is supplied from bin 10 by screw feeder 12 to mixing tank 14. Ethylene glycol is supplied to the mixing tank from glycol tank 16. The reactants are mixed to form a slurry by mixer 18 driven by motor 20. Slurry pump 22 feeds the slurry into recirculation pipe 24 leading from direct esterification reactor 26. The slurry feed mixes with reaction product and is heated to reaction temperature during passage through heat exchanger 28, and passes into the reactor. Liquid reaction product is withdrawn from the reactor through product line 30. Vapors containing ethylene glycol and water, plus small amounts of ester product and organic impurities formed in the reaction, separate in the reactor and pass through vapor line 32 to spray zone 34 at the bottom of rectifying column 36.

The rectifying column is preferably a bubble cap column having 5 to 20 (preferably about 12) plates. The vapor feed to the column is upward through bottom plate 38 from spray zone 34. The overhead vapors from top plate 40 are cooled by condenser 42 to form a distillate which collects in tank 44. Part of the distillate is returned to the top plate as reflux by pump 46. The remainder of the distillate is withdrawn to waste through line 48. Any residual vapor is purged to waste throught vent line 50 from the condenser. A reflux of about 40 to 70 percent of the total distillate is used to give a distillate containing less than 0.5 percent (preferably less than 0.05%) of ethylene glycol and a glycol condensate at the bottom of the column containing less than 10 percent water. The percent used as reflux will depend upon the composition of the vapor feed from the reactor. Adjustment is made by valve 52; automatic compensation for changes in vapor composition is provided by a conventional reflux rate controller 54 actuated by temperature transducer 56 at the bottom plate of the column.

Condensate from the bottom plate 38 passes downward through spray zone 34 and collects in hot well 58 along with condensed material from the spray. Condensate mixture is recirculated from the hot well by pump 60 to spray head 62, where it is sprayed at a temperature of 140° to 180° C. to partially cool the vapor feed, condense much of the glycol, and remove ester product which would otherwise cause fouling in the column. The amount of condensate spray is adjusted by valve 63 to maintain steady temperature conditions in the column. Glycol containing less than 10 percent water is recovered in the hot well and passes to treatment tank 64 for removal of solid materials. The recovered glycol is then returned to glycol tank 16, by line 66, for reuse in preparing slurry feed to the reactor. The rate at which recovered glycol is recycled is regulated by valve 68 to maintain a constant level in the hot well. Automation can be provided by a conventional flow controller 70 actuated by level switch 72. Glycol makeup is added to glycol tank 16 to replace glycol removed from the system as ester product.

The vapors leaving the top plate of the column are at a temperature of about 100°-102° C. They are liquified and cooled in condenser 42. The reflux to this plate is maintained at 35°-98° C. by adjusting the flow of cooling water to the condenser. The reflux ratio of liquid to vapor will depend upon the slurry feed mole ratio of ethylene glycol (2G) to terephthalic acid (TPA) fed to the reactor. Preferred reflux ratios for various slurry feed mole ratios are about as follows:

| 2G/TPA Reflux | 1.8 | 2.0 | 2.2 | 2.4 | 2.6 | 2.8 | 3.0 |
|---|---|---|---|---|---|---|---|
| ratio | 0.48 | 0.53 | 0.58 | 0.61 | 0.63 | 0.64 | 0.65 |

The liquid temperature at the bottom plate of the column depends upon the reflux ratio used. This temperature is normally within the range of 105° to 140° C. The condensate temperature in hot well 58 is at a higher temperature, since condensate is used to cool the vapor feed from the reactor. Hot well temperatures lower than about 155° C. will cause an undesirable amount of solids to form in the hot well. Undesirable glycol ether compounds are formed at increasing rates at higher temperatures. Preferred maximum hot well temperatures for various slurry feed mole ratios are about as follows:

| 2G/TPA | 1.8 | 2.0 | 2.2 | 2.4 | 2.6 | 2.8 | 3.0 |
|---|---|---|---|---|---|---|---|
| HWT(°C.) | 160 | 164 | 167 | 169 | 171 | 173 | 175 |

Sufficient heat is removed from the system by condenser 42 for operation under the above conditions without additional cooling of the hot well condensate. Adequate cooling of the vapor feed in the spray zone can be accomplished when condensate is used at a rate of 1 to 25 kilograms of spray per kilogram of slurry feed to the reactor.

EXAMPLE

Using apparatus of the type indicated in the drawing, 1,000 pounds (453.6 kg) of ethylene glycol (2G) per hour are mixed with 1,070 pounds (485.3 kg) of terephthalic acid (TPA) per hour to form a slurry, having a 2G/TPA mole ratio of 2.5, which is fed into the recirculation pipe of a reactor having an external heat exchanger. The slurry enters at the bottom of the heat exchanger and is heated to 305° C. in ester reaction product. The reactor pressure is 2.5 psig (17.2 kPag). The terephthalic acid is esterified to form an ester product having a relative viscosity (HRV) of 2.9 (corresponding to an average degree of polymerization of about 7), which is subsequently polymerized to an HRV of 21.5 to form polyester having excellent properties for spinning into textile filaments. Polyester filaments are spun, drawn and cut to make staple fiber of 4.25 denier with a high quality rating based on determinations of color and diethylene glycol content.

Excess glycol and other vapors separate from the ester product in the reactor and are fed to a spray zone at the bottom of the rectification column used for recovery of ethylene glycol. These hot feed vapors are sprayed with 5,500 pounds (2495 kg) per hour of hot-well condensate to cool the vapors to 163° C. and scrub out sublimed and entrained ester products which form solids at lower temperatures. The vapors then pass upward into a 12 plate, 15½ inch (39.4 cm) diameter, bubble cap column. Reflux at 95° C. is provided to the top plate at a rate of about 308 pounds (140 kg) per hour to recover substantially 100 percent of the ethylene glycol in the reactor vapors. The reflux rate is controlled by a temperature signal from the bottom plate. When the temperature increases, the reflux rate increases to maintain a hotwell condensate temperature of about 157° C. Likewise, when the temperature decreases, the reflux rate decreases. The following temperatures are measured for liquid on plates of the column:

| Plate | Plate | Plate |
|---|---|---|
| (1) 120° C. | (4) 102° C. | (10) 100.5° C. |
| (2) 106 | (8) 101 | (12) 100 |

Overhead vapors from the top plate have about the following composition in weight percent:

| Water | 98.13 |
|---|---|
| Ethylene glycol | 0.016 |
| Acetaldehyde | 1.05 |
| 2-methyl-1,3-dioxolane | 0.76 |
| 1,4-dioxane | 0.043 |

Condensed overhead vapors are used for reflux and the remaining distillate is taken to waste treatment at 250 pounds (113.4 kg) per hour. Uncondensed vapors are vented to a waste scrubber which uses 150 pounds (68 kg) of 8.2 pH water per hour to raise the pH of the mixture above 6.0. The less acidic pH facilitates waste treatment handling by reducing decomposition of 2-methyl-1,3-dioxolane.

The ethylene glycol in the feed vapors is recovered as hotwell condensate of about the following composition in weight percent:

| Ethylene glycol | 89.5 |
|---|---|
| Water | 5.6 |
| Solids | 4.5 |
| Diethylene glycol | 0.4 |

This glycol condensate is recovered at a rate of about 625 pounds (283 kg) per hour and is recycled for use in the slurry feed to the reactor without further purification. The "solids" content of the condensate is from sublimed and entrained ester products scrubbed out of the feed vapors by spraying with condensate. The spray treatment effectively avoids fouling in the column.

Relative viscosity (HRV) is the ratio of the viscosity of a solution of 0.8 gm of the polyester dissolved at room temperature in 10 ml of hexafluoroisopropanol containing 80 ppm $H_2SO_4$ to the viscosity of the $H_2SO_4$-containing hexafluoroisopropanol itself, both measured at 25° C. in a capillary viscosimeter and expressed in the same units.

I claim:

1. In a continuous direct esterification reaction process wherein a slurry feed of ethylene glycol and terephthalic acid in molar proportions of 1.5 to 4.0 glycol to 1.0 terephthalic acid is heated at 280° to 315° C. in reaction product to esterify the terephthalic acid and form an ester product having an average degree of polymerization of 2 to 10, and hot reaction vapors containing ethylene glycol and water plus small amounts of ester product and organic impurities are separated from the reaction product; the improvement for continuously recovering and reusing the ethylene glycol in said vapors which comprises conducting the hot reaction vapors into a spray zone at the bottom of a rectification column, condensing vapors obtained from the top of the column as an aqueous distillate, recycling about 40 to 70 weight percent of the aqueous distillate to the upper portion of the column to act as a reflux, whereby the aqueous distillate contains less than 0.5 weight percent ethylene glycol, collecting a glycol condensate at the bottom of the column containing less than 10 percent water, spraying the hot reaction vapors with some of the glycol condensate at 140° to 180° C. in the spray zone to maintain steady temperature conditions and to remove ester product and a large portion of the glycol from the vapors, and recycling glycol condensate to the slurry feed.

2. A process as defined in claim 1 wherein the rectification column has 5 to 20 plates.

3. A process as defined in claim 2 wherein the reflux is adjusted to maintain a steady temperature on the bottom plate within the range of 110° to 140° C.

4. A process as defined in claim 1 wherein the hot reaction vapors are sprayed with 1 to 25 kilograms of condensate per kilogram of slurry feed to the reaction.

5. A process as defined in claim 1 wherein the glycol condensate contains 2 to 7 weight percent water to reduce formation of ether compounds from glycol in the esterification reaction.

* * * * *